(12) United States Patent
Kaneko

(10) Patent No.: US 9,924,856 B2
(45) Date of Patent: Mar. 27, 2018

(54) ENDOSCOPE

(71) Applicant: OLYMPUS CORPORATION, Tokyo (JP)

(72) Inventor: Hiroyuki Kaneko, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/298,359

(22) Filed: Oct. 20, 2016

(65) Prior Publication Data

US 2017/0035282 A1 Feb. 9, 2017

Related U.S. Application Data

(63) Continuation of application No. PCT/JP2015/076155, filed on Sep. 15, 2015.

(30) Foreign Application Priority Data

Jan. 28, 2015 (JP) ................. 2015-014664

(51) Int. Cl.
*A61B 1/00* (2006.01)
*A61B 1/04* (2006.01)
(Continued)

(52) U.S. Cl.
CPC .............. *A61B 1/07* (2013.01); *A61B 1/0011* (2013.01); *A61B 1/00057* (2013.01);
(Continued)

(58) Field of Classification Search
CPC ....... A61B 1/07; A61B 1/307; A61B 1/00167; A61B 1/04; A61B 1/00057;
(Continued)

(56) References Cited

U.S. PATENT DOCUMENTS 4,272,156 A * 6/1981 Ishibashi ............ A61B 1/00117
385/117
2009/0048490 A1 2/2009 Iijima
2016/0195706 A1* 7/2016 Fujii .................. A61B 1/00096
362/551

FOREIGN PATENT DOCUMENTS

CN 102316783 A 1/2012
EP 2011428 A1 1/2009
(Continued)

OTHER PUBLICATIONS

International Search Report dated Dec. 1, 2015 issued in PCT/JP2015/076155.

*Primary Examiner* — Timothy J Neal
(74) *Attorney, Agent, or Firm* — Scully, Scott, Murphy & Presser, P.C.

(57) ABSTRACT

An endoscope includes: a first fiber provided with a first flat surface from which illuminating light is emitted; a pipe including a through hole to which a distal end portion of the first fiber is fixed and including a first surface that can be a flat surface identical to the first flat surface and a second surface which is a flat surface orthogonal to a central axis of the through hole; and a distal end component in which a stopper hole in which an end portion on the distal end side of the pipe is disposed is formed, the stopper hole including an abutting surface on which at least part of the second surface of the pipe abuts, on a bottom side, a concave portion which constitutes for obtaining a predetermined light distribution and is located closer to the front end side than the abutting surface.

8 Claims, 7 Drawing Sheets

(51) Int. Cl.
  *A61B 1/07* (2006.01)
  *A61B 1/018* (2006.01)
  *A61B 1/307* (2006.01)
  *G02B 23/24* (2006.01)

(52) U.S. Cl.
  CPC ...... *A61B 1/00071* (2013.01); *A61B 1/00096* (2013.01); *A61B 1/00105* (2013.01); *A61B 1/00128* (2013.01); *A61B 1/00135* (2013.01); *A61B 1/00142* (2013.01); *A61B 1/00167* (2013.01); *A61B 1/00195* (2013.01); *A61B 1/018* (2013.01); *A61B 1/04* (2013.01); *A61B 1/307* (2013.01); *G02B 23/2469* (2013.01); *G02B 23/243* (2013.01)

(58) Field of Classification Search
  CPC ............ A61B 1/00096; A61B 1/00105; A61B 1/0011; A61B 1/00128; A61B 1/00142; A61B 1/00195; A61B 1/018; G02B 23/2469; G02B 23/243
  See application file for complete search history.

(56) References Cited

FOREIGN PATENT DOCUMENTS

| | | |
|---|---|---|
| JP | 2007-054215 A | 3/2007 |
| JP | 2007-289355 A | 11/2007 |
| JP | 2009-207529 A | 9/2009 |
| WO | WO 2007122845 A1 | 11/2007 |
| WO | WO 2015/022774 A1 * | 2/2015 ............... A61B 1/00 |

* cited by examiner

ENDOSCOPE

CROSS REFERENCE TO RELATED APPLICATION

This application is a continuation application of PCT/JP2015/076155 filed on Sep. 15, 2015 and claims benefit of Japanese Application No. 2015-014664 filed in Japan on Jan. 28, 2015, the entire contents of which are incorporated herein by this reference.

BACKGROUND OF THE INVENTION

1. Field of the Invention

The present invention relates to an endoscope configured by fixing an end portion having an emission end face of a light guide fiber within a concave portion corresponding to an illuminating window portion formed of a transparent resin member.

2. Description of the Related Art

Endoscopes are widely used in medical and industrial fields. Examples of diagnostic or observation targets of an endoscope include interiors of a living body and a plant. For this reason, an endoscope apparatus requires a light source for illuminating a diagnostic or observation target.

A typical endoscope apparatus is provided with an endoscope and a light source apparatus as an endoscope external apparatus. The light source apparatus incorporates a light emission source that emits illuminating light such as a lamp or a light-emitting device.

The illuminating light emitted from the light emission source is transmitted by a light guide fiber provided in the endoscope and passes through an illuminating window provided at a distal end of an insertion portion to illuminate an observation target.

For example, Japanese Patent Application Laid-Open Publication No. 2009-207529 discloses an endoscope that can obtain a sufficient light quantity and a satisfactory light distribution, prevent losses in the light quantity, and has a small-diameter distal end. The distal end portion of the endoscope is formed of a transparent member through which illuminating light passes. The distal end portion is provided with an insertion part through which an observation optical system is inserted and an insertion portion into which a light guide fiber is inserted. A lens system having a predetermined function is formed at the distal end portion of the insertion portion.

According to Japanese Patent Application Laid-Open Publication No. 2009-207529, the insertion portion is disposed in a substantially annular shape so as to surround the insertion part. For this reason, the light guide fiber and the lens system are also disposed in a substantially annular shape so as to surround the observation optical system. The insertion portion is provided, on the proximal end side, with a prevention portion configured to prevent the distal end of the light guide fiber from being inserted as far as the distal end side of the lens system and dispose the fiber on the proximal end side of the lens system.

According to the configuration, when the light guide fiber is inserted into the insertion portion, the distal end of the fiber collides with the prevention portion, is thereby disposed at a predetermined position on the proximal end side, and stands face to face with the lens system.

As a result, when the light source apparatus emits irradiation light, the light guide fiber radiates the irradiation light from the distal end. The irradiation light radiated from the distal end is spread by the lens system, passes through the distal end portion, is radiated forward from a front end face side, passes through the distal end portion, enters a slope portion, is radiated from the slope portion side and illuminates interiors of a body cavity, thus enabling satisfactory observation.

SUMMARY OF THE INVENTION

An endoscope according to an aspect of the present invention includes a light guide fiber formed of a plurality of fiber elemental wires bundled into a predetermined shape and provided, at a distal end portion, with a first flat surface from which illuminating light is emitted, the first flat surface being formed inclined at an angle of less than 90 degrees with respect to a longitudinal axis, a pipe including a through hole to which a distal end portion side of the light guide fiber is fixed and a first surface that can be a flat surface identical to the first flat surface on a front end face, and a distal end member provided with a bottomed hole for an illumination optical system, the bottomed hole including a pipe disposing hole into which an end portion of the pipe on the distal end side is disposed and a concave portion constituting an irradiation lens system to obtain a predetermined light distribution.

According to the present invention described above, it is enabled to implement an endoscope that reduces the diameter of the insertion portion of the endoscope, prevents erroneous assembly and reliably, and easily achieves intended optical performance.

DETAILED DESCRIPTION OF THE PREFERRED EMBODIMENT(S)

Figure 1:
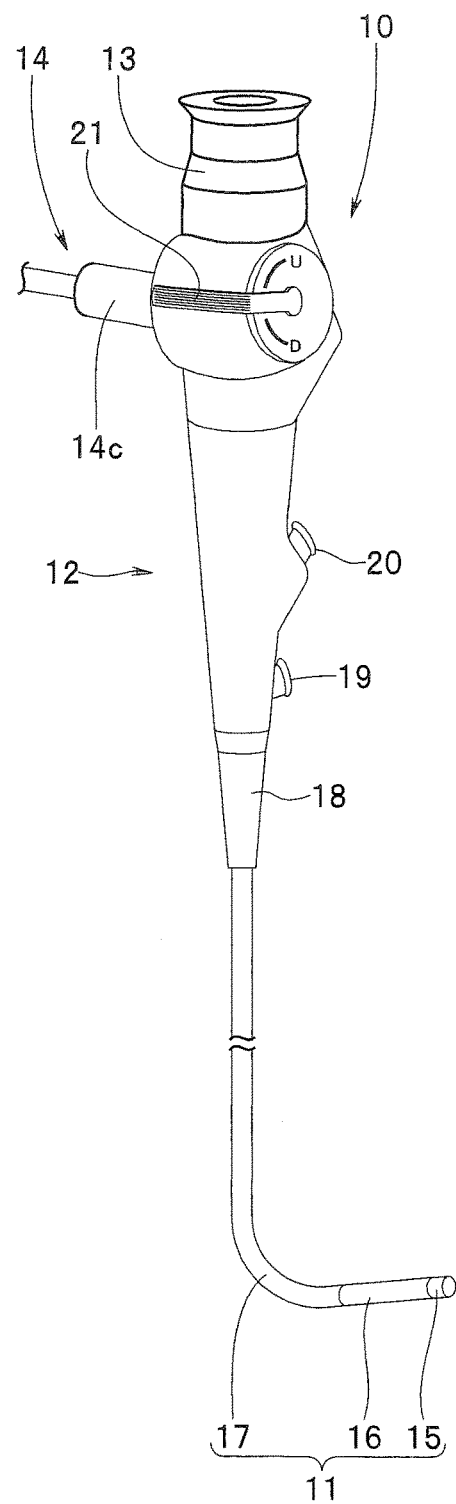
FIG. 1 is a diagram illustrating an endoscope.

Hereinafter, an embodiment of the present invention will be described with reference to the accompanying drawings.

Note that in the drawings used for the following description, components may be shown on different scales so that the respective components are shown in sizes in which they are recognizable on the respective drawings. Furthermore, the present invention is not limited to only quantities of the components, shapes of the components, size ratios among the components or relative positional relationships among the components illustrated in the drawings.

An endoscope 10 shown in FIG. 1 is, for example, a pyeloureteroscope, and is mainly constructed of an insertion portion 11, an operation section 12, and an eyepiece section 13. The eyepiece section 13 is provided on a proximal end side of the operation section 12.

Reference numeral 14 denotes a universal cord, and a connection connector 14c of the universal cord 14 is detachably attached to a light guide connection port (not shown) provided on a side of the operation section 12. The insertion portion 11 is constructed of, in the following order from the distal end side, a rigid distal end portion 15, a bending portion 16 configured to bend upward and downward, and a flexible tube portion 17 which is a tube body having flexibility.

A bend preventing portion 18 having predetermined elasticity is provided on a proximal end side of the flexible tube portion 17. The bend preventing portion 18 is provided so as to cover the proximal end portion of the flexible tube portion 17 to prevent buckling of the flexible tube portion 17 and is fixed so as to maintain water-tightness between the flexible tube portion 17 and a distal end side of the operation section 12.

The operation section 12 is provided with a water leakage detection pipe sleeve 19, a treatment instrument insertion port 20, and a bending operation lever 21 or the like. The bending operation lever 21 is freely rotatable. The bending portion 16 is bent in two directions, that is, upward and downward directions when a bending wire (not shown) is pulled or slackened as the lever 21 is turned.

Note that the bending portion 16 may be configured by providing an active bending portion that performs bending operation by pulling or slackening the bending wire and a passive bending portion that is bent by receiving an external force. The endoscope 10 is not limited to the pyeloureteroscope.

Figure 2:
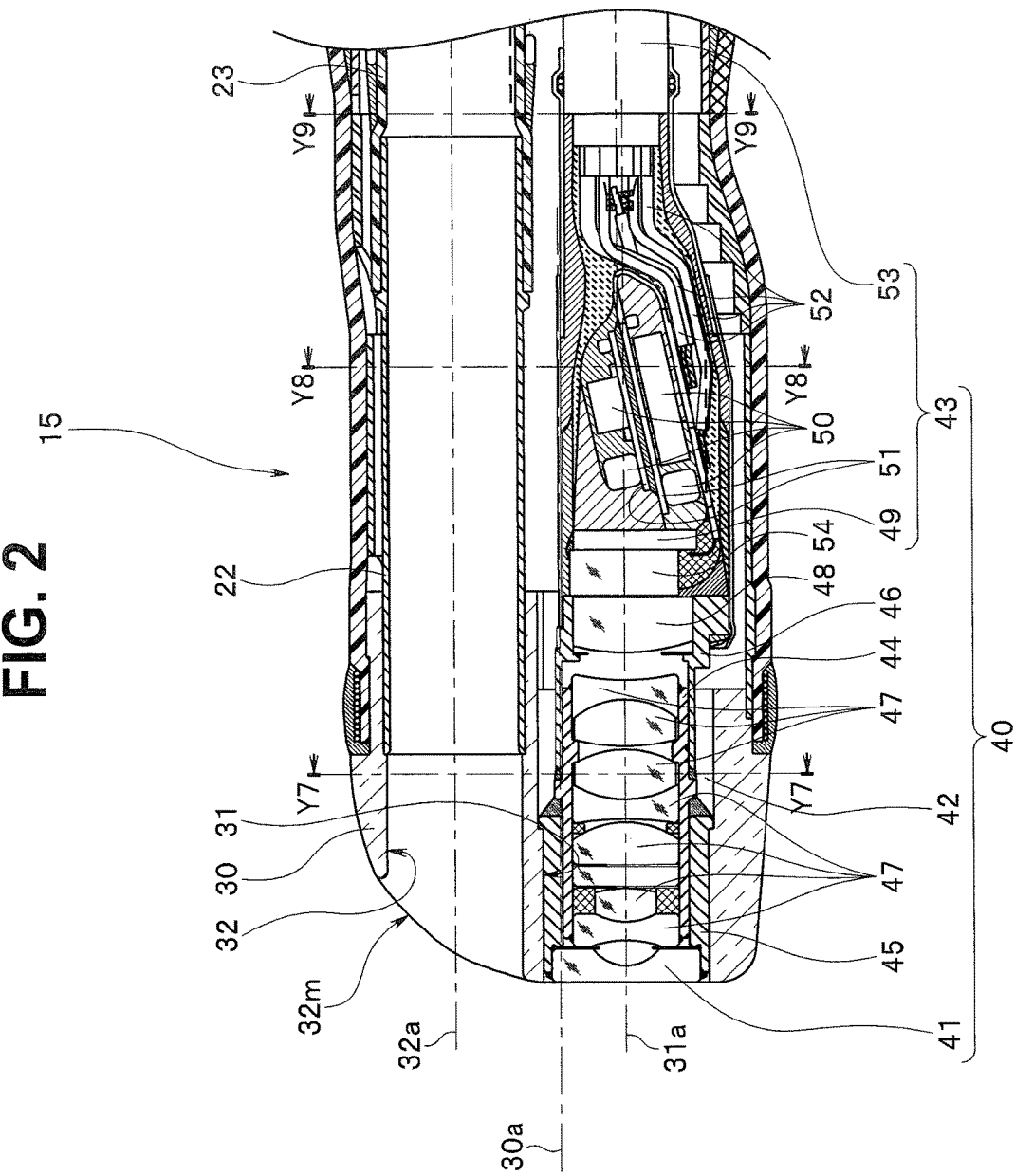
FIG. 2 is a cross-sectional view along a line Y2-Y2 indicated by arrows in FIG. 3.
Figure 3:
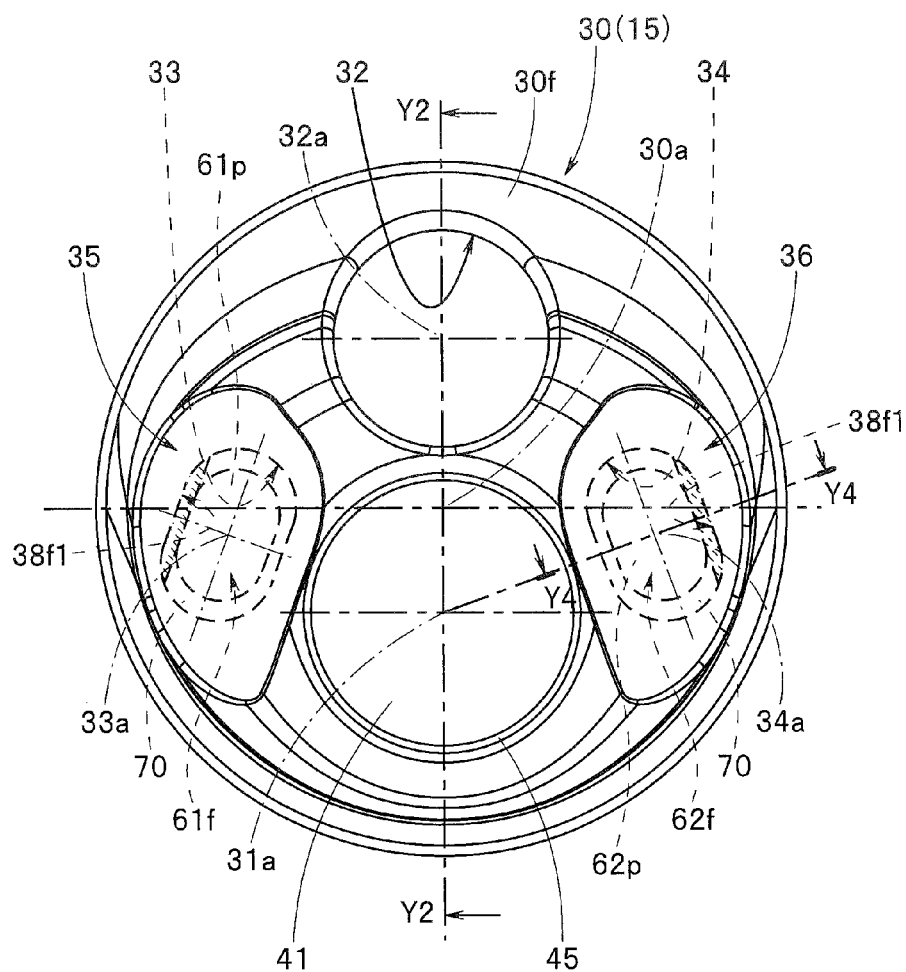
FIG. 3 is a front view of an insertion portion front end face.

In the present embodiment, the distal end portion 15 of the insertion portion 11 of the endoscope 10 is a cylindrical distal end member as shown in FIG. 2 and FIG. 3, and is a transparent resin member and configured as a distal end component 30.

The distal end component 30 includes a first through hole 31 having a first axis 31a parallel to a central axis 30a and a second through hole 32 having a second axis 32a as shown in FIG. 2, and two stopper holes 33 and 34 as shown in FIG. 3. Reference numeral 33a denotes a third axis parallel to the central axis 30a and reference numeral 34a denotes a fourth axis parallel to the central axis 30a.

Figure 4:
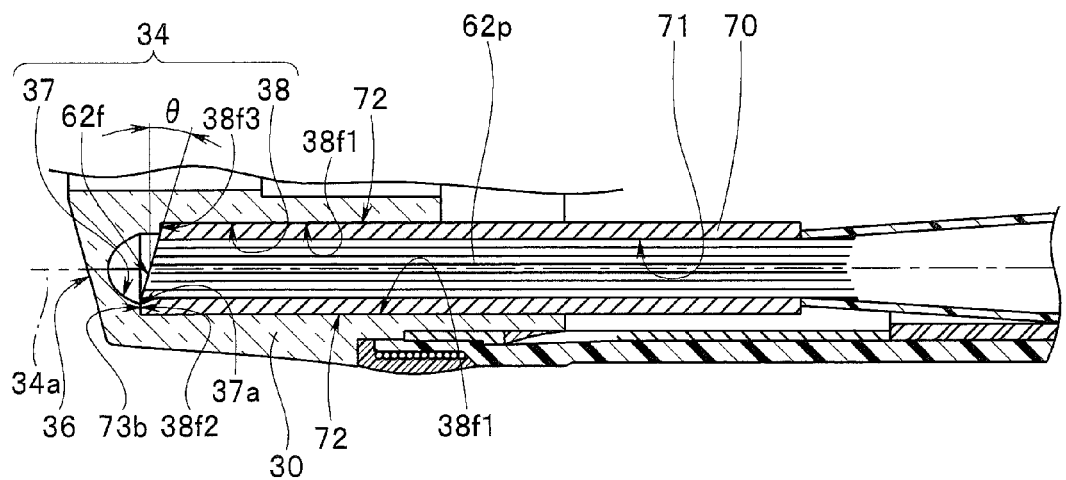
FIG. 4 is a cross-sectional view along a line Y4-Y4 indicated by arrows in FIG. 3.

The first through hole 31 shown in FIG. 2 is an image pickup optical system insertion hole having a stepped shape where a distal end side portion of an image pickup optical section 40 is fixed. The second through hole 32 is a treatment instrument channel hole and includes a distal end opening 32m. The stopper holes 33 and 34 shown by a broken line in FIG. 3 are bottomed holes for an illumination optical system and include a concave portion 37 and a pipe disposing hole 38 as shown in FIG. 4.

As shown in FIG. 2, the image pickup optical section 40 is mainly constructed of an observation lens 41, an objective optical system 42, and an image pickup apparatus 43.

Reference numeral 44 denotes a first lens frame, reference numeral 45 denotes a second lens frame, and reference numeral 46 denotes an image pickup frame.

The first lens frame 44 is provided with a plurality of types of optical lenses 47, a spacing ring (not shown), a diaphragm (not shown) and the like as optical members. The observation lens 41 and a distal end portion side of the first lens frame 44 are fixed to the second lens frame 45. A cover glass 48 which is an optical member and a proximal end portion side of the first lens frame 44 are fixed to the image pickup frame 46.

The image pickup apparatus 43 is constructed of a solid image pickup device 49 such as a CCD or C-MOS, a circuit substrate 51 mounted with a plurality of electronic parts 50, and a signal cable 53 that bundles a plurality of signal lines 52 into one line connected to the circuit substrate 51, or the like.

Reference numeral 54 denotes protective glass of the solid image pickup device 49 such as a CCD or C-MOS, a front end face of the protective glass 54 is bonded and fixed to the cover glass 48 with a transparent adhesive, and the proximal end face of the protective glass 54 is bonded and fixed to the image pickup surface side of the solid image pickup device 49 with a transparent adhesive.

A distal end portion of a tube pipe sleeve 22 is fixed into the second through hole 32. A distal end portion of a channel tube 23 is externally fitted and fixed to a proximal end portion of the tube pipe sleeve 22. The treatment instrument such as a biopsy needle introduced into the channel tube 23 in FIG. 2 from the treatment instrument insertion port 20 in FIG. 1 passes through the tube pipe sleeve 22, is introduced into the second through hole 32, and is then led out toward a target region from the distal end opening 32m.

As shown in FIG. 3, a second lens frame 45 to which the observation lens 41 of the image pickup optical section 40 is fixed is disposed at a predetermined position of a front end face 30f of the distal end component 30. Furthermore, the distal end opening 32m and a pair of illuminating window portions 35 and 36 having a predetermined shape are provided at predetermined positions of the front end face 30f. The pair of illuminating window portions 35 and 36 are disposed at predetermined positions with the image pickup optical section 40 positioned therebetween.

Note that a configuration including two or more illuminating window portions or a configuration including only one illuminating window portion may be adopted. The first illuminating window portion 35 is provided in correspondence with a first flat surface 61f which is an irradiation flat surface of a first fiber 61 which will be described later, and the second illuminating window portion 36 is provided in correspondence with a first flat surface 62f which is an irradiation flat surface of a second fiber 62 which will be described later. Reference numeral 70 denotes a pipe which will be described later.

Figure 5A:
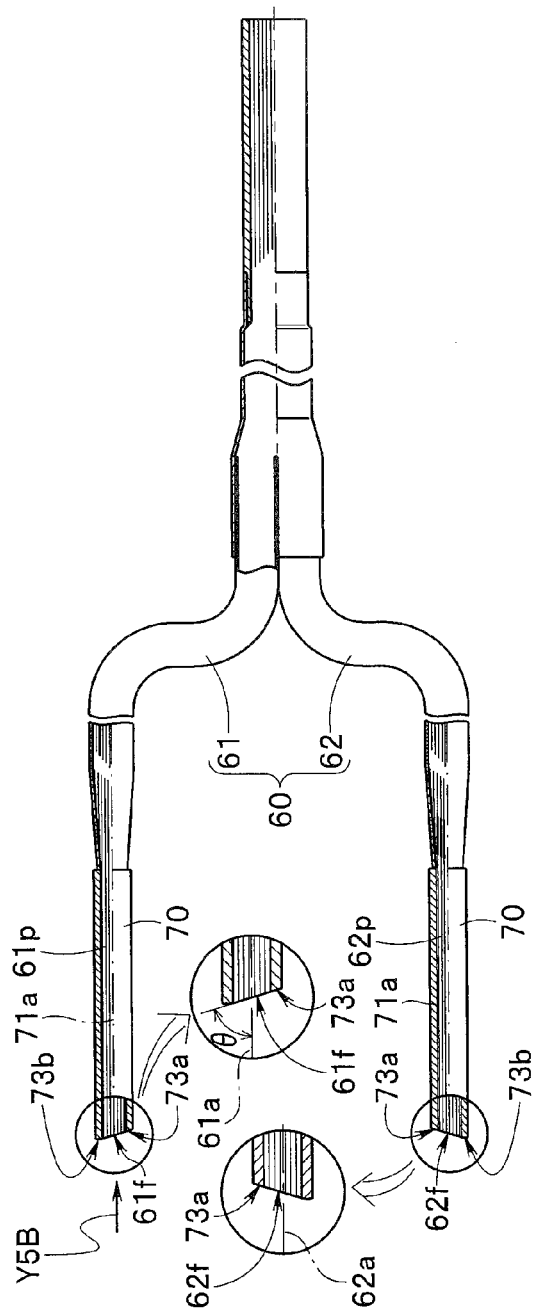
FIG. 5A is a diagram illustrating a light guide fiber.

As shown in FIG. 5(A), a light guide fiber 60 branches into, for example, a first fiber 61 and a second fiber 62 in the middle.

Figure 5B:
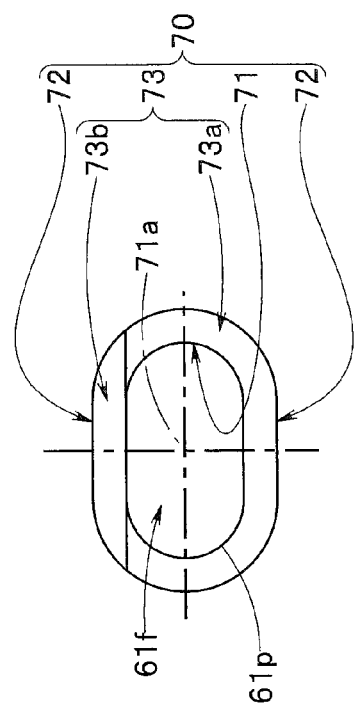
FIG. 5B is a front view of the light guide fiber.

As shown in FIG. 3 and FIG. 5(B), a distal end portion 61p of the first fiber 61 and a distal end portion 62p of the second fiber 62 are formed into a predetermined shape bundling a plurality of elemental wires in consideration of a light distribution, and have, for example, an oval shape made up of semi-circular portions making up both end portions and a rectangular portion located between the semi-circular portions.

As shown in FIG. 4 and FIG. 5(A), front end faces of the distal end portions 61p and 62p from which illuminating light is emitted are formed as the first flat surfaces 61*f* and 62*f* which are inclined at an angle θ. The first flat surfaces 61*f* and 62*f* are slopes inclined by an angle of less than 90 degrees with respect to longitudinal axes 61*a* and 62*a*.

In the present embodiment, the distal end portion 61*p* of the first fiber 61 and the distal end portion 62*p* of the second fiber 62 are fixed by bonding in a through hole 71 of the pipe 70 as shown in FIG. 4 and FIGS. 5(A) and 5(B).

The through hole 71 is formed such that the distal end portions 61*p* and 62*p* are engagedly disposed. That is, in the present embodiment, the pipe 70 has an oval external shape, and the flat surface portion is a positioning surface 72.

As shown in FIGS. 5(A) and 5(B), a front end face 73 of the pipe 70 has a first surface 73*a* and a second surface 73*b*. The first surface 73*a* is a flat surface that can be configured as one flat surface placed at an angle θ and identical to the first flat surface 61*f* of the distal end portion 61*p* and the first flat surface 62*f* of the distal end portion 62*p* disposed in the through hole 71 as shown in an enlarged view of the distal end portion in FIG. 5(A).

In contrast, the second surface 73*b* is a flat surface provided at a projecting end portion making up a distal-most end of the pipe 70 and orthogonal to a central axis 71*a* of the through hole 71.

Here, configurations of the first stopper hole 33 and the second stopper hole 34 will be described.

Note that the first stopper hole 33 and the second stopper hole 34 have a similar configuration. For this reason, the configuration of the second stopper hole 34 will be described with reference to FIG. 4 and FIG. 6(A), and description of the first stopper hole 33 is omitted.

Figure 6A:
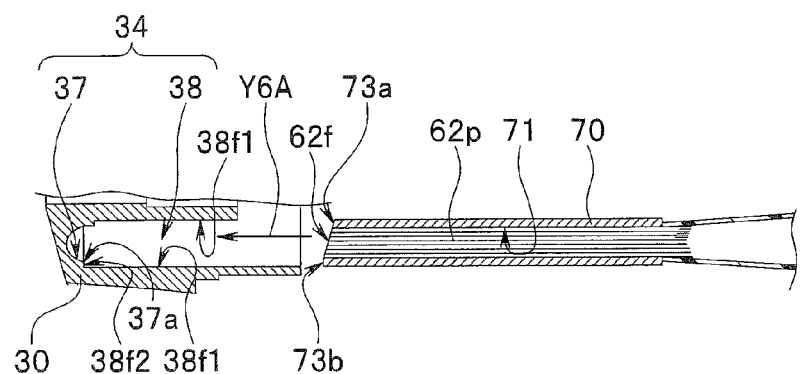
FIG. 6A is a diagram illustrating a step of disposing a pipe provided with a distal end portion of the light guide fiber in a pipe disposing hole of a stopper hole in a predetermined orientation.

As shown in FIG. 4 and FIG. 6(A), the second stopper hole 34 has a concave portion 37 and a pipe disposing hole 38.

A defining surface 38*f*1 and an abutting surface 38*f*2 are formed at predetermined positions of the pipe disposing hole 38. The defining surface 38*f*1 defines an arrangement position and an orientation of the pipe 70. The abutting surface 38*f*2 is provided at a distal end position of the defining surface 38*f*1 and defines an arrangement position in a fourth axis 34*a* direction.

The abutting surface 38*f*2 is formed so as to be located on an outer circumferential face side of the distal end component 30 (portion shown by hatching in FIG. 3). A first surface abutting surface 38*f*3 is formed at a position on the image pickup optical section 40 side at a predetermined distance from the abutting surface 38*f*2.

Note that the first surface 73*a* is formed so as to abut on a ridge line of the first surface abutting surface 38*f*3.

The abutting surface 38*f*2 is a flat surface on which the second surface 73*b* of the front end face 73 abuts, and the defining surface 38*f*1 is a flat surface on which the positioning surface 72 abuts.

The concave portion 37 is provided so as to be located closer to the second illuminating window portion 36 side than the abutting surface 38*f*. The surface side of the second illuminating window portion 36 and the bottom surface of the concave portion 37 each have a shape formed in consideration of a light distribution. An irradiation lens system having a predetermined light distribution characteristic is configured by providing the second illuminating window portion 36 and the concave portion 37 in the transparent distal end component 30.

An opening of a peripheral portion 37*a* of the concave portion 37 is set to be greater than an outside shape of the second fiber 62 disposed in the through hole 71 of the pipe 70 and smaller than an outside shape of the pipe 70. In other words, the opening region of the peripheral portion of the concave portion 37 is set to be wider than the illuminating light irradiation region of the first flat surface 62*f*.

As shown in FIG. 6(A), the pipe 70 where the distal end portion 62*p* of the second fiber 62 is disposed inside the through hole 71 is inserted through the pipe disposing hole 38 of the second stopper hole 34 as shown by an arrow Y6A with the second surface 73*b* being oriented toward the outer circumferential side of the distal end component 30 as shown in FIG. 6(A).

Figure 6B:
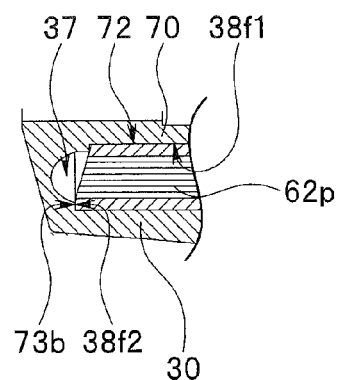
FIG. 6B is a diagram illustrating a state in which the pipe provided with the distal end portion of the light guide fiber is disposed in the pipe disposing hole of the stopper hole in the predetermined orientation.

When the abutting surface 38*f*2 is located on the outer circumferential face side of the distal end component 30 and if it is visually confirmed from the outer circumferential face side that the second surface 73*b* is arranged so as to abut on the abutting surface 38*f*2 as shown in FIG. 6(B), the pipe 70 where the distal end portion 62*p* of the second fiber 62 is provided is fixed to the distal end component 30 with an adhesive.

In the fixed state, the first flat surface 62*f* of the distal end portion 62*p* of the second fiber 62 disposed inside the pipe 70 is disposed on the bottom surface of the concave portion 37 in a predetermined state. That is, the orientation of the first flat surface 62*f* is defined with respect to the illumination lens system.

Figure 7:
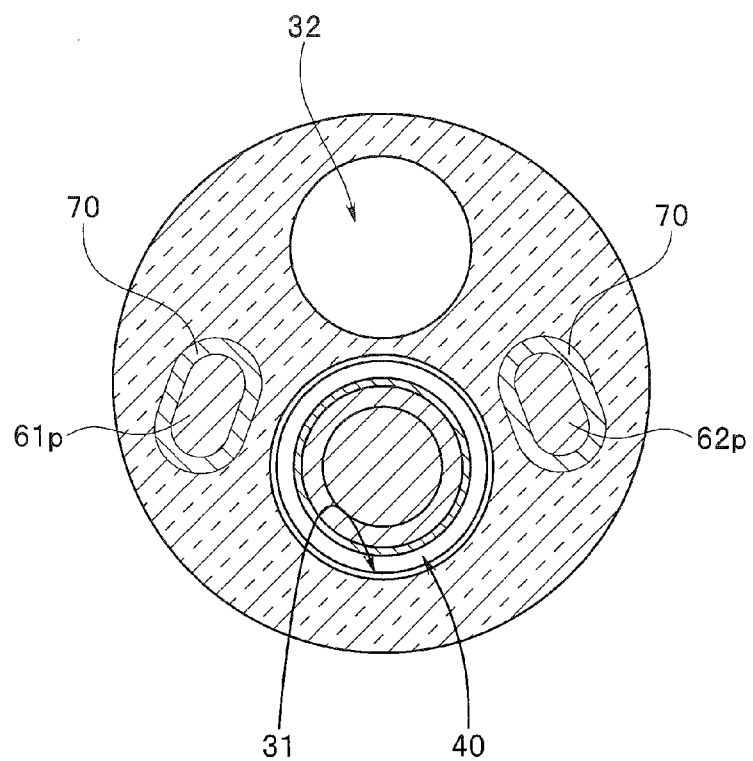
FIG. 7 is a cross-sectional view along a line Y7-Y7 indicated by arrows in FIG. 2.
Figure 8:
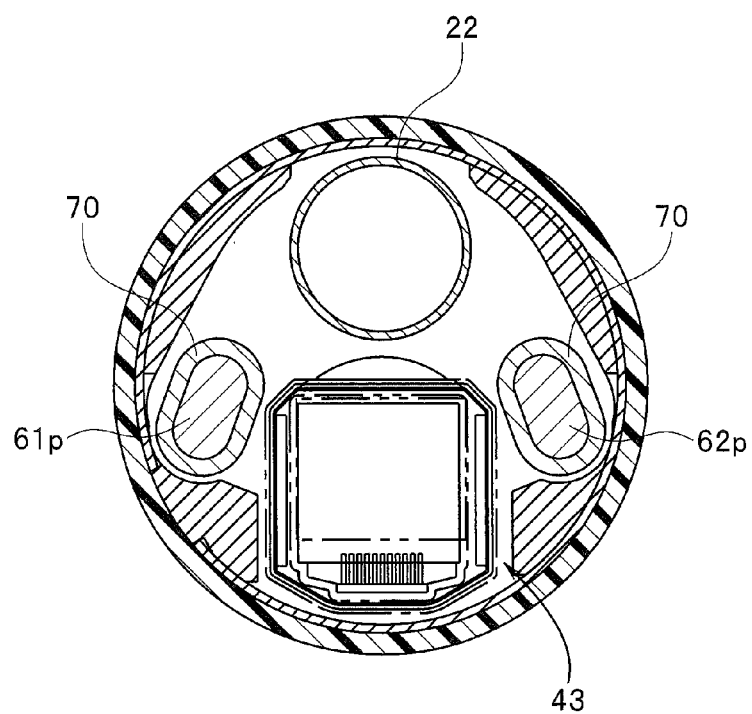
FIG. 8 is a cross-sectional view along a line Y8-Y8 indicated by arrows in FIG. 2.
Figure 9:
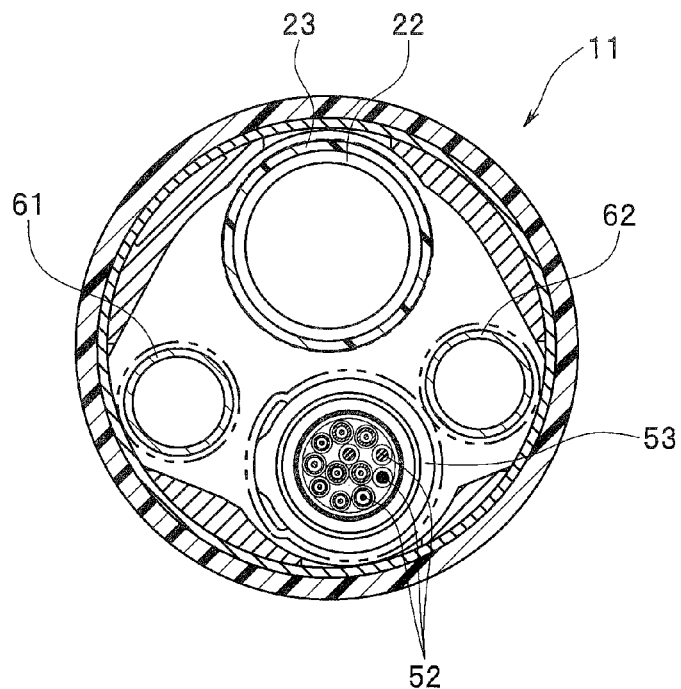
FIG. 9 is a cross-sectional view along a line Y9-Y9 indicated by arrows in FIG. 2.

The first fiber 61 and the second fiber 62 are disposed along an inner surface of the insertion portion 11 as shown in FIG. 7 to FIG. 9.

When irradiation light is emitted from the light source apparatus, the illuminating light is transmitted by the light guide fiber 60 provided in the endoscope 10 to the distal end portions 61*p* and 62*p* of the fibers 61 and 62 provided in a predetermined state on the distal end side of the insertion portion 11, and is radiated from the first flat surface 61*f* and the first flat surface 62*f*.

The illuminating light beams radiated from the first flat surfaces 61*f* and 62*f* are spread by the concave portion 37 which is an irradiation lens system, pass through the transparent distal end component 30, and are radiated from the illuminating window portions 35 and 36 into the body cavity to illuminate the observation region with an appropriate light distribution.

As a result, the image pickup optical section 40 picks up an image of the observation region illuminated with the illuminating light, and intended optical performance is thereby achieved and a satisfactory endoscope image is displayed on a screen of a display apparatus which is not shown.

Figure 10A:
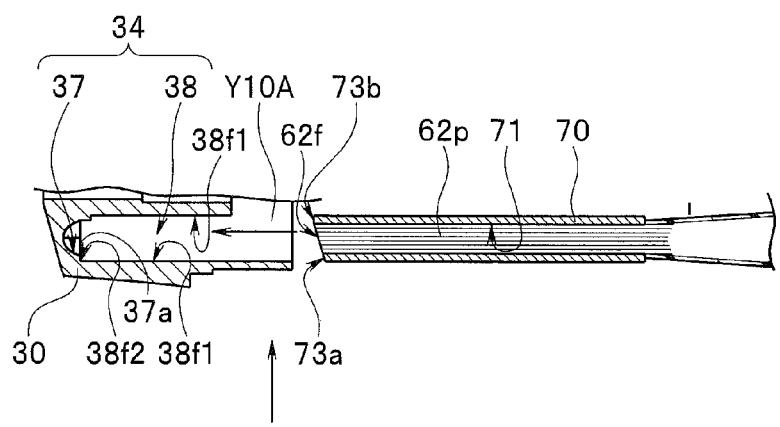
FIG. 10A is a diagram illustrating a case where the pipe provided with the distal end portion of the light guide fiber is disposed in the pipe disposing hole of the stopper hole in a wrong orientation.
Figure 10B:
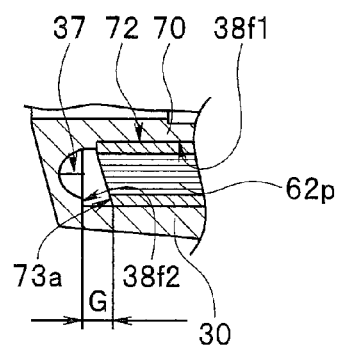
FIG. 10B is a diagram illustrating a state in which the pipe provided with the distal end portion of the light guide fiber is disposed in the pipe disposing hole of the stopper hole in a wrong orientation.

Note that as shown in FIG. 10(A), when the pipe 70 where the distal end portion 62*p* of the second fiber 62 is disposed inside the through hole 71 is oriented toward, for example, the image pickup optical section 40 side, which is different from the orientation shown in FIG. 6(A), and if the pipe 70 is inserted into the pipe disposing hole 38 of the second stopper hole 34 as shown by an arrow Y10A, the pipe 70 is disposed without the first surface 73*a* abutting on the abutting surface 38*f*2 but is located away from the abutting surface 38*f*2 by a distance G as shown in FIG. 10(B). For this reason, it is enabled to visually confirm the presence or absence of a gap from the outer circumferential face of the distal end component 30 and easily determine whether or not the components are erroneously assembled.

Thus, it is enabled to reduce the diameter of the insertion portion 11 by providing a plurality of illuminating window portions at predetermined positions with put the image pickup optical section 40 positioned therebetween without disposing the light guide fiber 60 in an annular shape so as to surround the image pickup optical section 40.

Furthermore, an irradiation lens system having a predetermined light distribution characteristic is configured by providing the illuminating window portions 35 and 36 on the surface side of the transparent distal end component 30, providing the concave portion 37 corresponding to the illuminating window portions 35 and 36 on the bottom surface of the stopper holes 33 and 34 provided on the distal end component 30. The pipe 70 is disposed in a predetermined state in which the distal end portions 61p and 62p of the light guide fiber 60 with a light distribution taken into consideration are disposed at predetermined positions in the stopper holes 33 and 34. That is, the positioning surface 72 of the pipe 70 is caused to abut on the defining surface 38f1 and the second surface 73b of the front end face 73 is caused to abut on the abutting surface 38f2.

In addition, since the opening of the peripheral portion 37a of the concave portion 37 is set to be greater than the outside shape of the fibers 61 and 62, and smaller than the outside shape of the pipe 70, it is enabled to prevent the fiber 61 from being arranged on the abutting surface 38f2. That is, the peripheral portion opening region of the concave portion 37 is set to be wider than the illuminating light irradiation region of the first flat surface 62f.

As a result, it is enabled to dispose the first flat surface 61f of the first fiber 61 and the first flat surface 62f of the second fiber 62 disposed in the pipe 70 in a predetermined state for the irradiation lens system, radiate preset illuminating light from each of the first flat surfaces 61f and 62f of the fibers 61 and 62, and radiate the illuminating light with an appropriate light distribution from the illuminating window portions 35 and 36 into the body cavity to illuminate the observation region.

Furthermore, since the front end face 73 is configured by providing the first surface 73a that forms a flat surface matching the slope of the fiber 61 in addition to the second surface 73b in the pipe 70, it is enabled to visually confirm the presence or absence of a gap between the first surface 73a and the abutting surface 38f2 from the outer circumferential face side of the distal end component 30 and prevent erroneous assembly.

Note that in the aforementioned embodiment, the distal end component 30 is made of a transparent member. However, the distal end component 30 may be molded from a transparent first resin member and a light-shielding second resin member. In this configuration, the range from the illuminating window portions 35 and 36 to the concave portion 37 is made of the transparent first resin member and a periphery of the range is made of the second resin member.

The first resin member and the second resin member may be either separate components or an integrated component through two-color molding.

Regarding the distal end member, the distal end component 30 is not limited to one made of resin, but may be one configured with a transparent member formed on a metallic distal end component or one provided with a distal end cover member molded through two-color molding as described above.

In this configuration, the stopper holes 33 and 34 are provided in the distal end cover member and the metallic distal end component, and the concave portion 37 and the abutting surface 38f2 are provided in the stopper holes 33 and 34 on the distal end cover member side.

In the aforementioned embodiment, the two positioning surfaces 72 are provided on the outer circumferential face of the pipe 70 so that the pipe 70 has an oval external shape. However, the external shape of the pipe 70 is not limited to the oval shape but may also be, for example, a D-figured shape.

That is, at least one positioning surface 72 may be provided on the outer circumferential face of the pipe 70 or the pipe 70 may have a rectangular shape in which the positioning surface provided on one side of the outer circumferential face of the pipe 70 is different from the positioning surface provided on the other side.

Note that the present invention is not limited to only the aforementioned embodiment, but may be modified in various ways without departing from the spirit and scope of the invention.

What is claimed is:

1. An endoscope comprising:
   an insertion portion having a distal end and a proximal end, the insertion portion being elongated along a longitudinal axis;
   a light guide fiber inserted along the longitudinal axis of the insertion portion, the light guide fiber comprising a plurality of fiber elemental wires bundled into a predetermined shape and comprising, at a distal end portion, a first flat surface from which illuminating light is emitted, the first flat surface being formed inclined at an angle of less than 90 degrees with respect to the longitudinal axis;
   a pipe comprising a through hole to which a distal end portion side of the light guide fiber is fixed, the pipe including on a front end face thereof, a first surface in a flat surface identical to the first flat surface and a second surface, the second surface being a flat surface orthogonal to a central axis of the through hole; and
   a distal end member disposed at the distal end of the insertion portion, the distal end member being provided with a channel for an illumination optical system, the channel comprising a pipe disposing hole into which an end portion of the pipe on a distal end side is disposed and a concave portion comprising an irradiation lens system to obtain a predetermined light distribution,
   wherein the pipe disposing hole comprises an abutting surface on which at least part of the second surface of the pipe abuts.

2. The endoscope according to claim 1, wherein the concave portion is a bottom surface of the channel located closer to the distal end side than the abutting surface of the pipe disposing hole.

3. The endoscope according to claim 2, wherein the distal end member is a distal end cover member and comprises at least:
   an image pickup optical system insertion hole configured to dispose an image pickup optical section; and
   at least one channel for an illumination optical system disposed at a predetermined position with respect to the image pickup optical system insertion hole.

4. The endoscope according to claim 1, wherein the second surface of the pipe is formed at a projecting end portion of the first surface.

5. The endoscope according to claim 1, wherein
   the pipe comprises, on an outer circumferential face, at least one flat surface provided along a central axis of the through hole, and
   the pipe disposing hole comprises a defining surface which is a flat surface on which the flat surface of the pipe abuts, the defining surface defining an orientation of the first surface with respect to the illumination lens system.

6. The endoscope according to claim 1, wherein an opening of a peripheral portion of the concave portion is set to be greater than an outside diameter of the fiber disposed in the through hole of the pipe and smaller than an outside diameter of the pipe.

7. The endoscope according to claim 1, wherein a region of an opening of a peripheral portion of the concave portion is wider than an irradiation region of light on the first flat surface of the light guide fiber.

8. An endoscope comprising:

an insertion portion having a distal end and a proximal end, the insertion portion being elongated along a longitudinal axis;

a light guide fiber inserted along the longitudinal axis of the insertion portion, the light guide fiber comprising a plurality of fiber elemental wires bundled into a predetermined shape and comprising, at a distal end portion, a first flat surface from which illuminating light is emitted, the first flat surface being formed inclined at an angle of less than 90 degrees with respect to the longitudinal axis;

a pipe comprising a through hole to which a distal end portion side of the light guide fiber is fixed, the pipe including on a front end face thereof, a first surface in a flat surface identical to the first flat surface; and a distal end member disposed at the distal end of the insertion portion, the distal end member being provided with a channel for an illumination optical system, the channel comprising a pipe disposing hole into which an end portion of the pipe on a distal end side is disposed and a concave portion comprising an irradiation lens system to obtain a predetermined light distribution, wherein an opening of a peripheral portion of the concave portion is set to be greater than an outside diameter of the fiber disposed in the through hole of the pipe and smaller than an outside diameter of the pipe.

* * * * *